United States Patent
Morimoto et al.

(10) Patent No.: US 9,955,947 B2
(45) Date of Patent: May 1, 2018

(54) DEVICE AND METHOD FOR SHIELDING AN ULTRASOUND PROBE

(75) Inventors: Atsushi Morimoto, Tokyo (JP); Scott Kerwin, Scottsdale, AZ (US)

(73) Assignee: General Electric Company, Schenectady, NY (US)

( * ) Notice: Subject to any disclaimer, the term of this patent is extended or adjusted under 35 U.S.C. 154(b) by 2695 days.

(21) Appl. No.: 11/183,063

(22) Filed: Jul. 15, 2005

(65) Prior Publication Data
US 2007/0016059 A1    Jan. 18, 2007

(51) Int. Cl.
*A61B 8/14*    (2006.01)
*A61B 8/00*    (2006.01)

(52) U.S. Cl.
CPC .............. *A61B 8/14* (2013.01); *A61B 8/4455* (2013.01)

(58) Field of Classification Search
USPC ....... 600/459, 407, 437, 442, 443, 444, 445, 600/446, 447, 448, 449, 462, 463
See application file for complete search history.

(56) References Cited

U.S. PATENT DOCUMENTS

| | | | |
|---|---|---|---|
| 4,455,873 A | | 6/1984 | Abts |
| 5,634,466 A | * | 6/1997 | Gruner .......................... 600/459 |
| 5,721,463 A | | 2/1998 | Synder |
| 6,142,947 A | * | 11/2000 | Tran et al. .................... 600/459 |
| 6,340,352 B1 | | 1/2002 | Okada et al. |
| 6,771,074 B2 | | 8/2004 | Zou et al. |
| 6,776,758 B2 | | 8/2004 | Peszynski et al. |
| 7,022,081 B2 | * | 4/2006 | Oliver ........................... 600/459 |
| 2001/0021807 A1 | * | 9/2001 | Saito et al. ................... 600/437 |
| 2003/0073906 A1 | * | 4/2003 | Flesch et al. ................. 600/459 |
| 2004/0073118 A1 | * | 4/2004 | Peszynski et al. ............ 600/459 |
| 2005/0124889 A1 | * | 6/2005 | Flesch ........................... 600/445 |

* cited by examiner

*Primary Examiner* — Michael Kahelin
*Assistant Examiner* — Shahdeep Mohammed
(74) *Attorney, Agent, or Firm* — Joseph M. Butscher; The Small Patent Law Group, LLC

(57) ABSTRACT

A device and method for shielding an ultrasound probe are provided. The ultrasound probe includes a handle having an interior chamber with an open front end and a transducer assembly provided in the chamber. The transducer assembly converts acoustic energy received through the open front end to electrical signals. The ultrasound probe further includes a shielding portion provided between the transducer assembly and an exterior of the handle.

4 Claims, 7 Drawing Sheets

DEVICE AND METHOD FOR SHIELDING AN ULTRASOUND PROBE

BACKGROUND OF THE INVENTION

This invention relates generally to ultrasound systems, and more particularly, to a device and method for shielding a probe of the ultrasound system.

Ultrasound systems typically include ultrasound scanning devices, such as, ultrasound probes having different control components and transducers that allow for performing various different ultrasound scans (e.g., different imaging of a volume or body). These ultrasound probes may include control components within different portions of the probe, including, for example, the probe handle and the probe connection member for connecting to an ultrasound system. These control components within the probe allow for controlling operation of the probe by an ultrasound system, for example, to operate in different modes, such as, amplitude mode (A-mode), brightness mode (B-1 mode), power Doppler mode, color imaging mode, among others.

Ultrasound probes may be used in connection with or in proximity to other equipment. For example, an ultrasound probe may be used in connection with a stress test in which it is in proximity to a treadmill. This other electrical equipment may generate electrical noise, and more particularly, electromagnetic interference (EMI) noise that can interfere with the operation of the ultrasound probe. Specifically, the ultrasound probe will receive not only acoustic noise, namely, echoes from ultrasonic waves transmitted from the probe, but also EMI noise and/or signals. This EMI noise from the other equipment can degrade or destroy the quality of an image acquired by the ultrasound probe.

Thus, current probe designs may not adequately protect or shield against interference, and more particularly, EMI noise generated by equipment in proximity to the ultrasound probe.

BRIEF DESCRIPTION OF THE INVENTION

In one embodiment, an ultrasound probe is provided that includes a handle having an interior chamber with an open front end and a transducer assembly provided in the chamber. The transducer assembly converts acoustic energy received through the open front end to electrical signals. The ultrasound probe further includes a shielding portion provided between the transducer assembly and an exterior of the handle.

In another embodiment, a probe handle is provided that includes a housing having an interior chamber configured to receive an electronics subassembly, with the housing having an open front end. The probe handle further includes an electromagnetic shielding portion covering the open front end.

In yet another embodiment, a method for shielding a probe includes providing an electromagnetic shielding portion between a transducer assembly and an exterior of a handle of the probe.

DETAILED DESCRIPTION OF THE INVENTION

Exemplary embodiments of ultrasound probes providing shielding are described in detail below. In particular, a detailed description of exemplary ultrasound systems is first provided followed by a detailed description of various embodiments of ultrasound probes.

Figure 1:
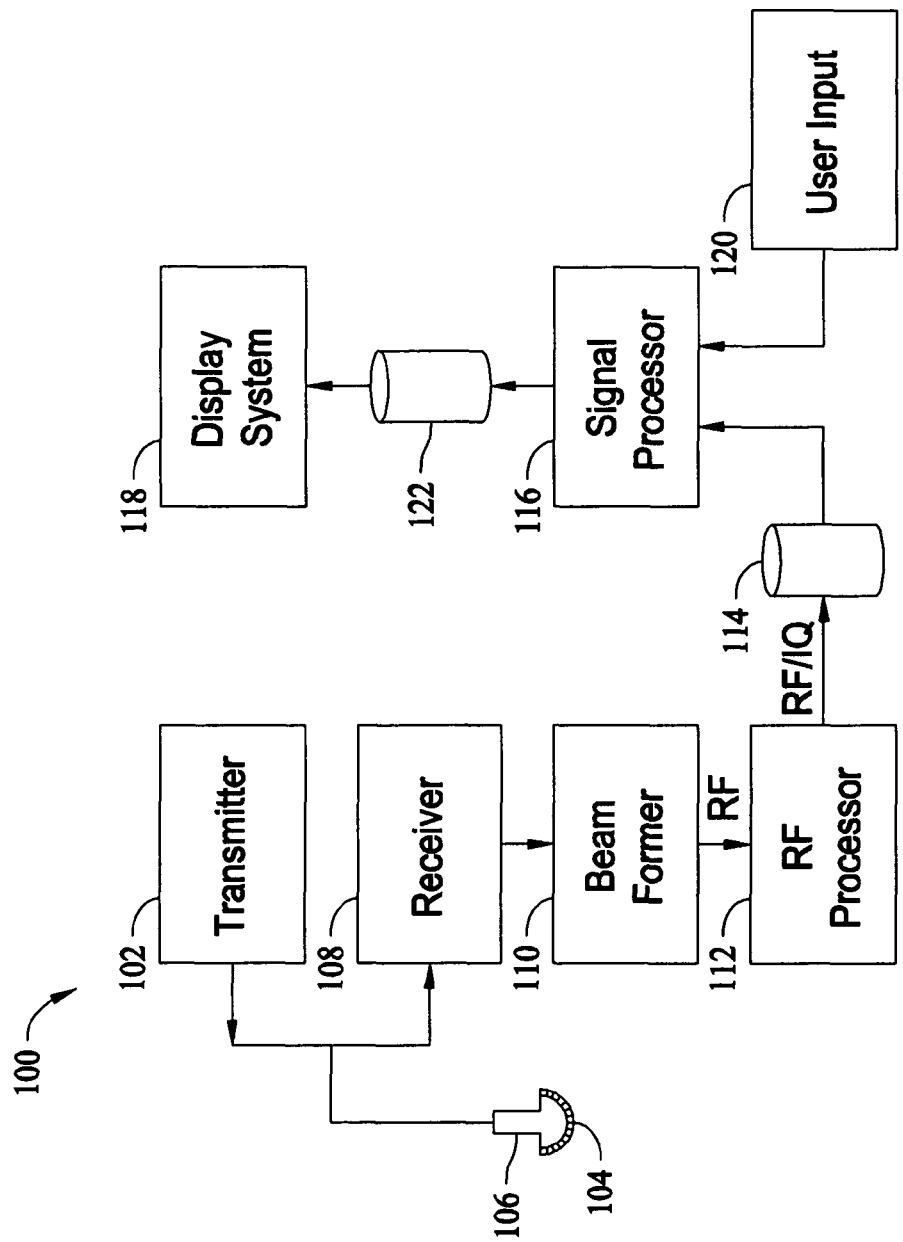
FIG. 1 is a block diagram of an ultrasound system in accordance with an exemplary embodiment of the present invention.

FIG. 1 illustrates a block diagram of an exemplary embodiment of an ultrasound system 100 that may be used, for example, to acquire and process ultrasonic images. The ultrasound system 100 includes a transmitter 102 that drives an array of elements 104 (e.g., piezoelectric crystals) within or formed as part of a transducer 106 to emit pulsed ultrasonic signals into a body or volume. A variety of geometries may be used and one or more transducers 106 may be provided as part of a probe (not shown). The pulsed ultrasonic signals are back-scattered from density interfaces and/or structures, for example, in a body, like blood cells or muscular tissue, to produce echoes that return to the elements 104. The echoes are received by a receiver 108 and provided to a beamformer 110. The beamformer performs beamforming on the received echoes and outputs an RF signal. The RF signal is then processed by an RF processor 112. The RF processor 112 may include a complex demodulator (not shown) that demodulates the RF signal to form IQ data pairs representative of the echo signals. The RF or IQ signal data then may be routed directly to an RF/IQ buffer 114 for storage (e.g., temporary storage).

The ultrasound system 100 also includes a signal processor 116 to process the acquired ultrasound information (i.e., RF signal data or IQ data pairs) and generate frames of ultrasound information for display on a display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information is displayed on the display system 118 at a slower frame-rate. An image buffer 122 may be included for storing processed frames of acquired ultrasound information that are not scheduled to be displayed immediately. In an exemplary embodiment, the image buffer 122 is of sufficient capacity to store at least several seconds of frames of ultrasound information. The frames of ultrasound information may be stored in a manner to facilitate retrieval thereof according to their order or time of acquisition. The image buffer 122 may comprise any known data storage medium.

A user input device 120 may be used to control operation of the ultrasound system 100. The user input device 120 may be any suitable device and/or user interface for receiving user inputs to control, for example, the type of scan or type of transducer to be used in a scan.

Figure 2:
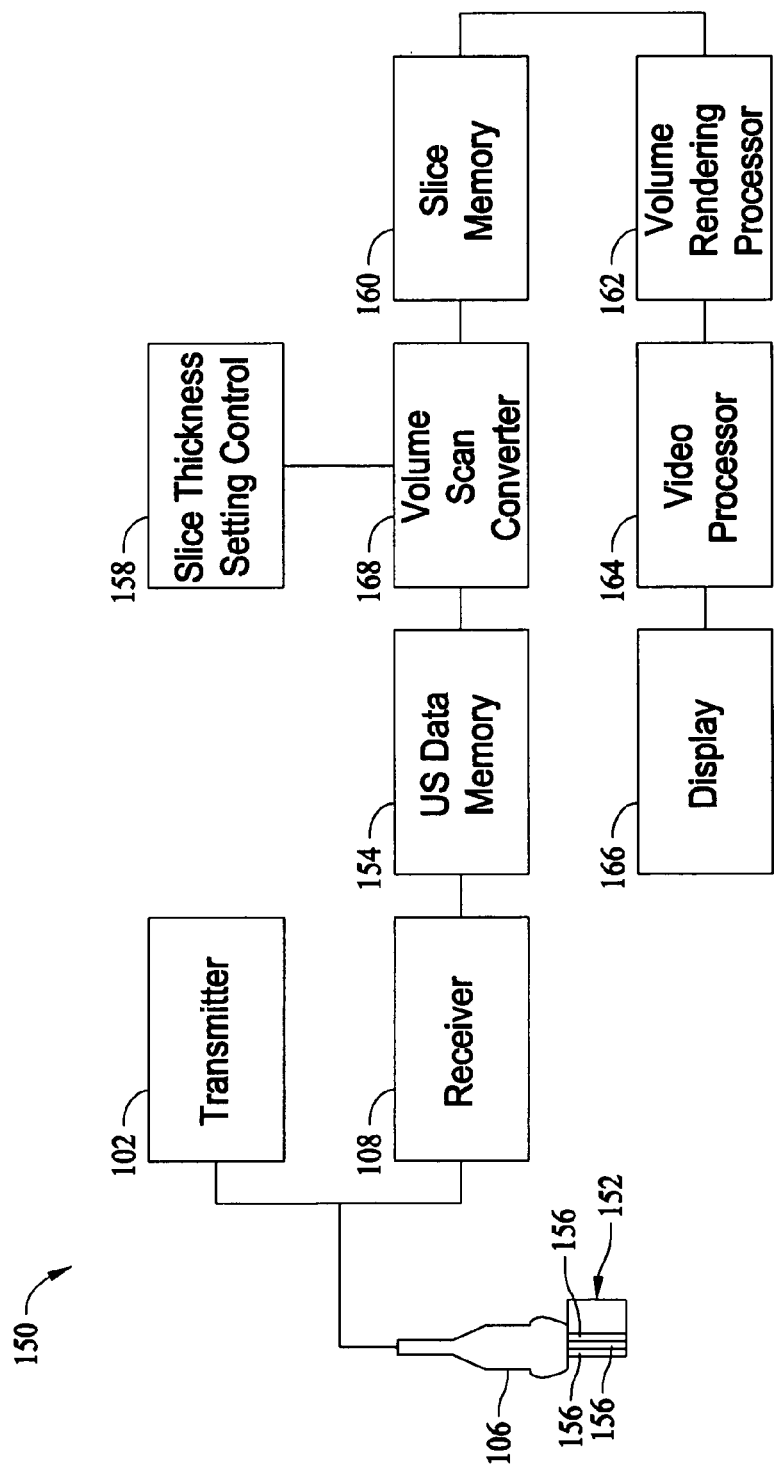
FIG. 2 is a block diagram of an ultrasound system in accordance with another exemplary embodiment of the present invention.

FIG. 2 illustrates a block diagram of another exemplary embodiment of an ultrasound system 150 that may be used, for example, to acquire and process ultrasonic images. The ultrasound system 150 includes the transducer 106 in communication with the transmitter 102 and receiver 108. The transducer 106 transmits ultrasonic pulses and receives echoes from structures inside a scanned ultrasound volume 152. A memory 154 stores ultrasound data from the receiver 108 derived from the scanned ultrasound volume 152. The scanned ultrasound volume 152 may be obtained by various techniques, including, for example, 3D scanning, real-time 3D imaging, volume scanning, scanning with transducers having positioning sensors, freehand scanning using a Voxel correlation technique, 2D scanning or scanning with a matrix of array transducers, among others.

The transducer 106 is moved, such as along a linear or arcuate path, while scanning a region of interest (ROI). At each linear or arcuate position, the transducer 106 obtains a plurality of scan planes 156. The scan planes 156 are collected for a thickness, such as from a group or set of adjacent scan planes 156. The scan planes 156 are stored in the memory 154, and then provided to a volume scan converter 168. In some exemplary embodiments, the transducer 106 may obtain lines instead of the scan planes 156, with the memory 154 storing lines obtained by the transducer 106 rather than the scan planes 156. The volume scan converter 168 receives a slice thickness setting from a slice thickness setting control 158, which identifies the thickness of a slice to be created from the scan planes 156. The volume scan converter 168 creates a data slice from multiple adjacent scan planes 156. The number of adjacent scan planes 156 that are obtained to form each data slice is dependent upon the thickness selected by the slice thickness setting control 158. The data slice is stored in a slice memory 160 and accessed by a volume rendering processor 162. The volume rendering processor 162 performs volume rendering upon the data slice. The output of the volume rendering processor 162 is provided to a video processor 164 that processes the volume rendered data slice for display on a display 166.

It should be noted that the position of each echo signal sample (Voxel) is defined in terms of geometrical accuracy (i.e., the distance from one Voxel to the next) and one or more ultrasonic responses (and derived values from the ultrasonic response). Suitable ultrasonic responses include gray scale values, color flow values, and angio or power Doppler information.

It should be noted that the ultrasound systems 100 and 150 may include additional or different components. For example, the ultrasound system 150 may include a user interface or user input 120 (shown in FIG. 1) to control the operation of the ultrasound system 150, including, to control the input of patient data, scan parameters, a change of scan mode, and the like.

Figure 3:
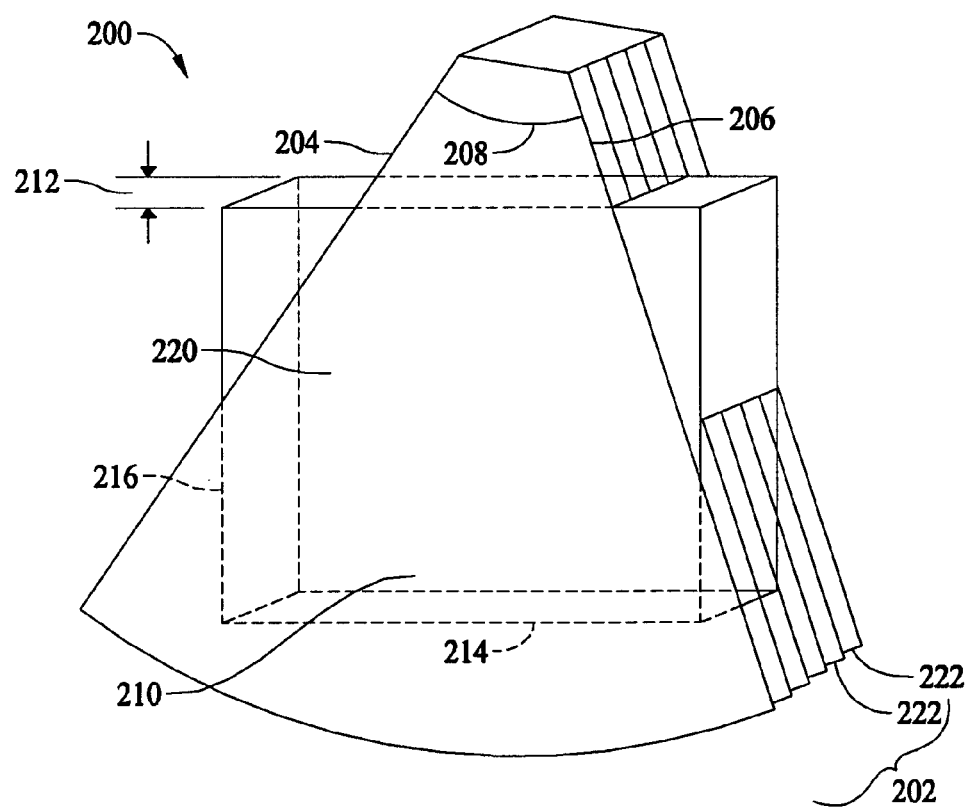
FIG. 3 is a perspective view of an image of an object acquired by the systems of FIGS. 1 and 2 in accordance with an exemplary embodiment of the present invention.

FIG. 3 illustrates an exemplary image of an object 200 that may be acquired by the ultrasound systems 100 and 150. The object 200 includes a volume 202 defined by a plurality of sector shaped cross-sections with radial borders 204 and 206 diverging from one another at an angle 208. The transducer 106 (shown in FIGS. 1 and 2) electronically focuses and directs ultrasound firings longitudinally to scan along adjacent scan lines in each scan plane 156 (shown in FIG. 2) and electronically or mechanically focuses and directs ultrasound firings laterally to scan adjacent scan planes 156. The scan planes 156 obtained by the transducer 106, and as illustrated in FIG. 1, are stored in the memory 154 and are scan converted from spherical to Cartesian coordinates by the volume scan converter 168. A volume comprising multiple scan planes 156 is output from the volume scan converter 168 and stored in the slice memory 160 as a rendering region 210. The rendering region 210 in the slice memory 160 is formed from multiple adjacent scan planes 156.

The rendering region 210 may be defined in size by an operator using a user interface or input to have a slice thickness 212, width 214 and height 216. The volume scan converter 168 (shown in FIG. 2) may be controlled by the slice thickness setting control 158 (shown in FIG. 2) to adjust the thickness parameter of the slice to form a rendering region 210 of the desired thickness. The rendering region 210 defines the portion of the scanned ultrasound volume 152 that is volume rendered. The volume rendering processor 162 accesses the slice memory 160 and renders along the slice thickness 212 of the rendering region 210.

Referring now to FIGS. 1 and 2, during operation, a slice having a pre-defined, substantially constant thickness (also referred to as the rendering region 210) is determined by the slice thickness setting control 158 and is processed in the volume scan converter 168. The echo data representing the rendering region 210 (shown in FIG. 3) may be stored in the slice memory 160. Predefined thicknesses between about 2 mm and about 20 mm are typical, however, thicknesses less than about 2 mm or greater than about 20 mm may also be suitable depending on the application and the size of the area to be scanned. The slice thickness setting control 158 may include a control member, such as a rotatable knob with discrete or continuous thickness settings.

The volume rendering processor 162 projects the rendering region 210 onto an image portion 220 of an image plane(s) 222 (shown in FIG. 3). Following processing in the volume rendering processor 162, pixel data in the image portion 220 may be processed by the video processor 164 and then displayed on the display 166. The rendering region 210 may be located at any position and oriented at any direction within the volume 202. In some situations, depending on the size of the region being scanned, it may be advantageous for the rendering region 210 to be only a small portion of the volume 202.

Figure 4:
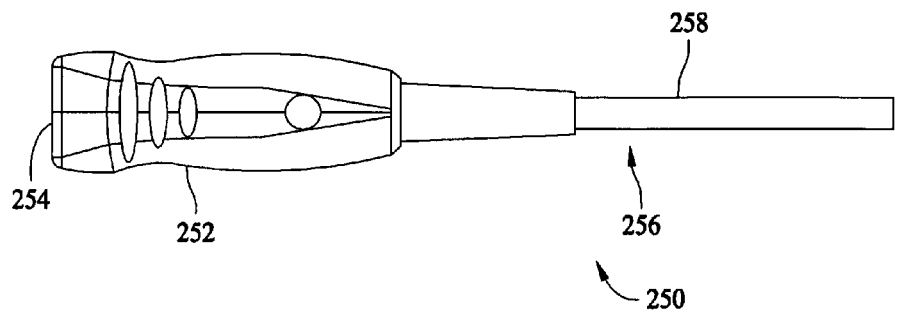
FIG. 4 is a bottom plan view of an exemplary ultrasound probe constructed in accordance with an embodiment of the invention.
Figure 5:
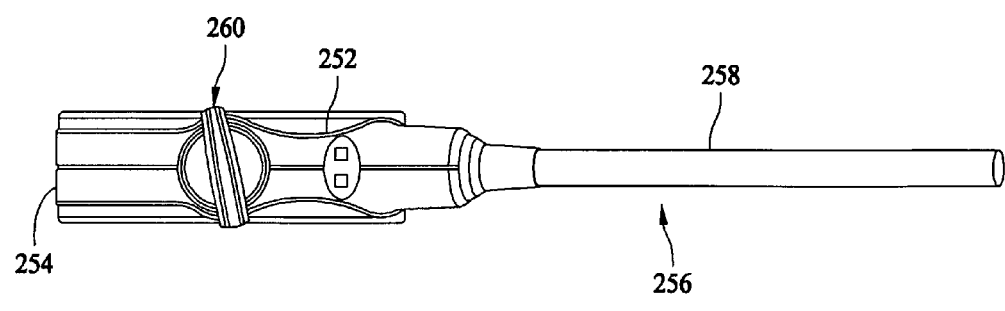
FIG. 5 is a top plan view of an exemplary ultrasound probe constructed in accordance with an embodiment of the invention.
Figure 6:
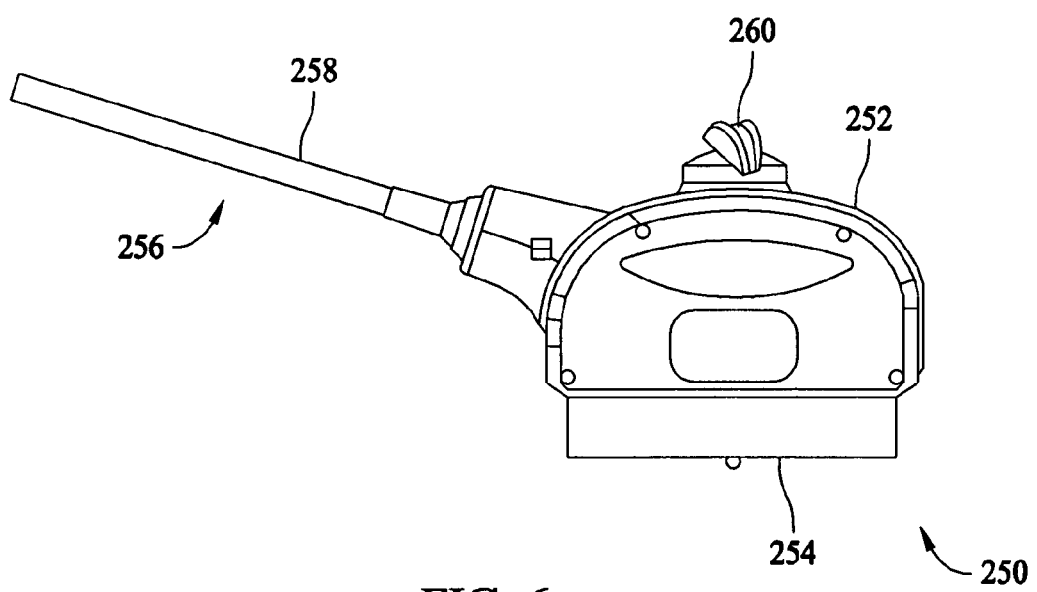
FIG. 6 is a side elevation view of an exemplary ultrasound probe constructed in accordance with an embodiment of the invention.

FIGS. 4 through 6 illustrate an ultrasound probe 250 constructed in accordance with an exemplary embodiment of the invention. The ultrasound probe 250 generally includes a housing 252 having a scan portion 254 and a connection portion 256. The housing 252 generally includes therein control components and operating components for performing ultrasound scans. For example, and in general, the housing 256 may include therein a transducer array (not shown) having a plurality of elements, such as, for example, piezoelectric elements (not shown) and control components, for example, electrical components mounted to a printed circuit board (not shown). The scan portion 254 is used to scan, for example, a patient, by emitting therefrom ultrasonic waves and receiving echoes as is known. The connection portion 256 includes a system cable 258 for connection to, for example, a ultrasound system scanning controller via a connection (not shown) as is known.

It should be noted that the ultrasound probe 250 may include additional component parts, for example, a control knob 260. The control knob 260 is rotatable between an engaged and a disengaged position to control operation of the ultrasound probe 250.

Figure 7:
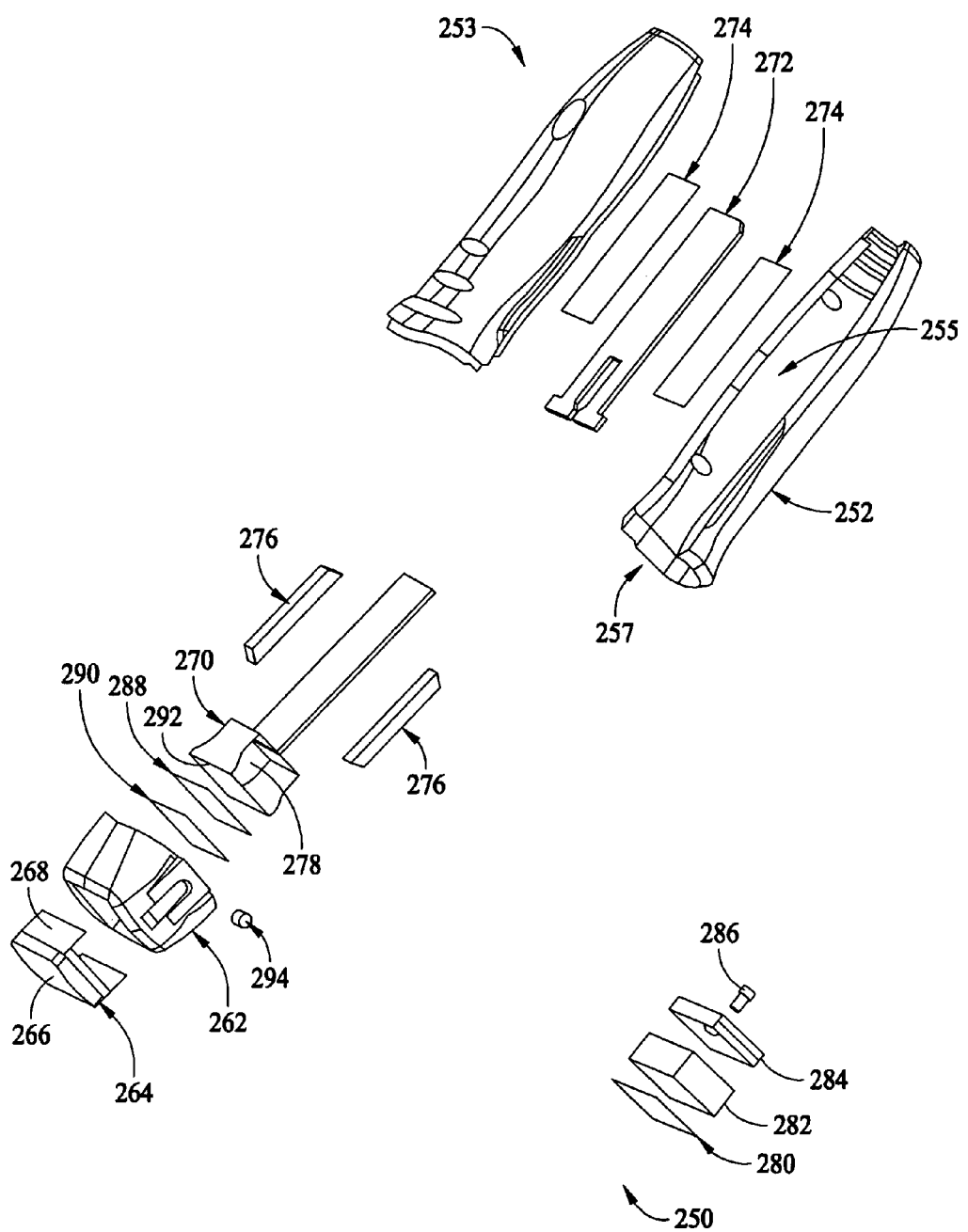
FIG. 7 is an exploded view of an exemplary ultrasound probe constructed in accordance with an embodiment of the invention.

One exemplary probe 250 constructed in accordance with an embodiment of the present invention is shown in FIG. 7. The probe 250 includes the housing 252, which in this embodiment is formed in a two piece design and generally forms a handle portion 253 of the ultrasound probe 250. The two pieces may be secured together using screws, adhesive, and/or other securing means as are known and form an interior chamber 255 having an open front end 257. The interior chamber 255 may be configured to receive therein, for example, an electronics subassembly as is known and be surrounded by electromagnetic shielding. The probe 250 at the scan portion 254 generally includes a nosepiece 262 (having a recess on a back side thereof) and a lens assembly 264. In one exemplary embodiment, the lens assembly 264 includes a lens 266 formed of silicon and a shielding portion 268 (e.g., a planar shielding portion) formed of copper. In this embodiment, the silicon lens 266 and copper shielding portion 268 are formed using a molding process (e.g., comolded) to provide a bonded construction. For example, a copper foil may be bonded to a silicon lens using an injection molding process. However, it should be noted that other materials may be used for constructing the lens assembly 264. For example, the shielding portion 268 may be formed of gold, aluminum or tin. Additionally, the shielding portion 268 may be formed in shapes other than an open-backed box as shown, for example, as a flat planar member as described in more detail below.

The ultrasound probe 250 also includes a connection member 270, which in one embodiment is a flexible printed circuit board. The connection member 270 may be formed of multiple layers, and includes a portion for receiving therebetween a plate 272. The connection member 270 may be connected to the plate 272, for example, using pressure sensitive adhesive tape 274. Connectors 276 also may be provided as part of the connection member 270 for interfacing and connection therewith.

The connection member 270 also may form an opening 278 for receiving therein a ceramic composite 280, a backing strip 282 and a block 284, together forming a transducer assembly as is known. A screw 286 or other securing member also may be provided for connecting or securing the various components together. A first matching layer 288 and a second matching layer 290 may be provided on a mounting surface 292 of the connection member 270.

Figure 8:
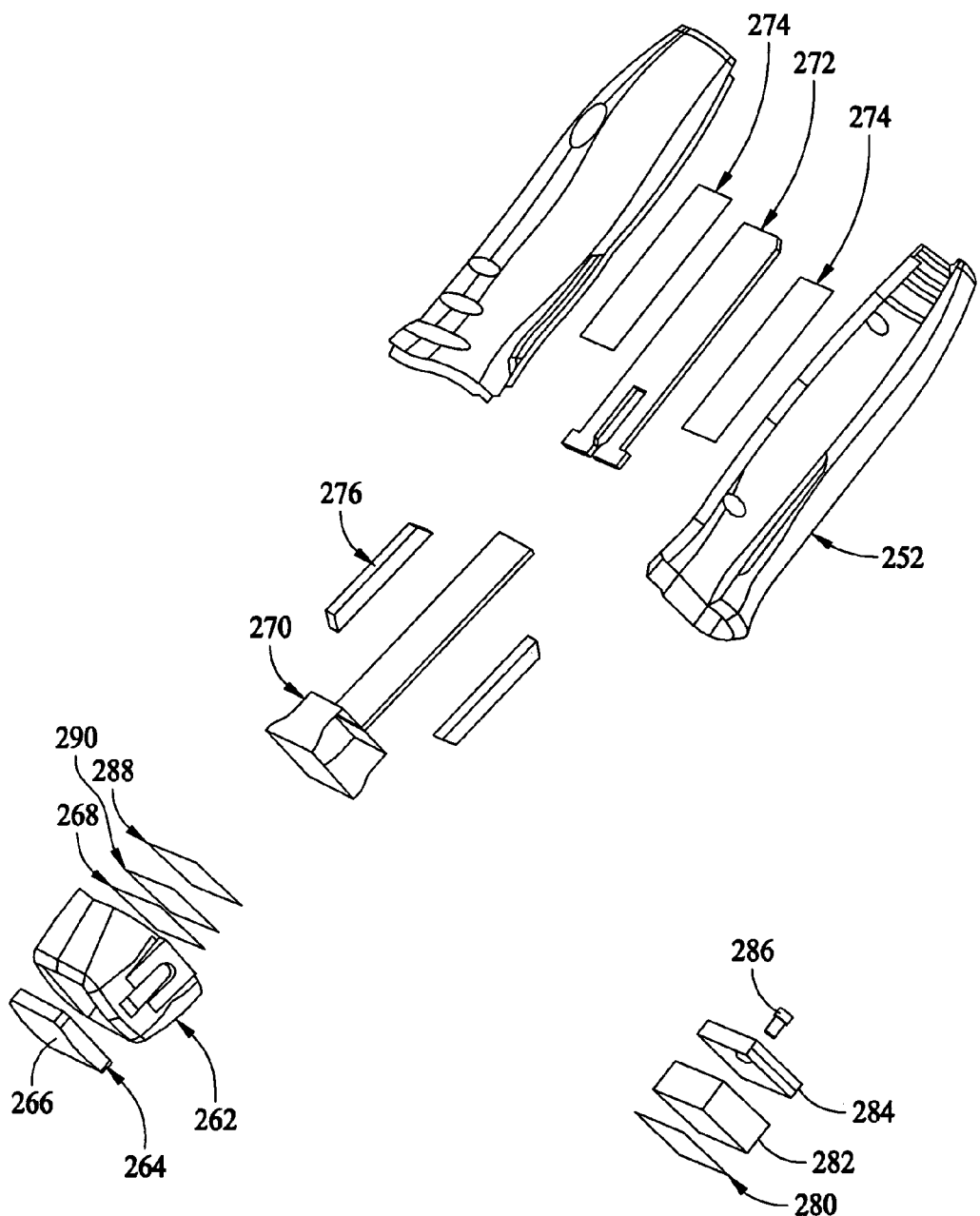
FIG. 8 is an exploded view of exemplary ultrasound probe constructed in accordance with another embodiment of the invention.

It should be noted that the shielding portion 268 may be modified as desired or needed. For example, the shielding portion 268 may be formed as a separate portion (e.g., separate copper foil), and laminated, for example, using an epoxy, to the lens assembly 264 as shown in the probe 250 of FIG. 8. Thus, the shielding portion is still provided between the lens 266 and the transducer assembly. Additionally, the shielding portion 268 may be configured for positioning in different portions of the probe 250. For example, in an exemplary embodiment the shielding portion 268 may be provided (e.g., metalized) along the length of the lens 266. In another exemplary embodiment, the shielding portion 268 may be provided (e.g., metalized) to the transducer assembly of the probe 250. In still another exemplary embodiment, the shielding portion may be provided (e.g., metalized) between matching layers of the transducer assembly of the probe 250.

Additional components also may be provided as desired or needed. For example, a light emitting diode (LED) 294 for indicating an operating status (e.g., on or off) for the ultrasound probe 250 may be provided.

Thus, various embodiments of the present invention provide an ultrasound probe having shielding, for example, to shield from EMI noise. The probe includes a shielding portion provided generally between an open front end of a handle of the ultrasound probe, which may have a lens, and a transducer array. This shielding portion shields the transducer array from, for example, EMI noise. It should be noted that the various embodiments of probes described herein are not limited to a particular application, but may be used in different applications as desired or needed, for example, in medical imaging, non-destructive testing and/or sonar evaluation.

While the invention has been described in terms of very specific embodiments, those skilled in the art will recognize that the invention can be practiced with modification within the spirit and scope of the claims.

What is claimed is:

1. An ultrasound probe, comprising:
   a handle having an interior chamber with an open front end;
   a transducer assembly provided in said chamber, said transducer assembly converting acoustic energy received through said open front end to electrical signals;
   a lens covering said open front end and having sides; and
   a shielding layer coupled to and extending along a length of an inner surface of the lens covering and rearwardly beyond the sides of the lens covering, the shielding layer shaped and sized for insertion through the open front end and extending within the handle over the transducer assembly when the lens is coupled to the open front end; wherein said transducer assembly comprises a matching layer and a ceramic layer having a flex circuit therebetween, said shielding layer covering said matching layer.

2. An ultrasound probe, comprising:
   a handle having an interior chamber with an open front end;
   a transducer assembly provided in said chamber, said transducer assembly converting acoustic energy received through said open front end to electrical signals;
   a lens covering said open front end and having sides; and
   a shielding layer coupled to and extending along a length of an inner surface of the lens covering and rearwardly beyond the sides of the lens covering, the shielding layer shaped and sized for insertion through the open front end and extending within the handle over the transducer assembly when the lens is coupled to the open front end;
   wherein said lens having a recess in a back-side thereof, and said shielding layer and a front end of transducer assembly fitting into said recess.

3. A probe handle, comprising: a housing having an interior chamber configured to receive an electronics subassembly, said housing having an open front end; and a lens assembly covering said open front end; and means for shielding the electronics subassembly from electromagnetic interference, wherein said lens assembly having a recess in a back-side thereof, said means for shielding and a front end of said electronics subassembly fitting into said recess.

4. A method for shielding a probe, said method comprising: providing an electromagnetic shielding portion metalized on and along a length of a lens of a probe and continuing rearwardly extending from the lens into a handle of the probe; and configuring the electromagnetic shielding portion for insertion through an open front end of the handle of the probe as part of the lens when the lens is coupled to a nosepiece.

* * * * *